United States Patent [19]

Nakagawa et al.

[11] Patent Number: 4,952,804
[45] Date of Patent: Aug. 28, 1990

[54] ELECTRON DIFFRACTION METHOD OF DETERMINING THE DEGREE OF FATIGUE FOR METALLIC MATERIALS

[75] Inventors: Yukiya G. Nakagawa; Hisae Yoshizawa, both of Tokyo, Japan

[73] Assignee: Electric Power Research Institute, Inc., Palo Alto, Calif.

[21] Appl. No.: 295,857

[22] Filed: Jan. 11, 1989

[51] Int. Cl.$^5$ .................................. H01J 37/30
[52] U.S. Cl. ........................ 250/307; 250/311
[58] Field of Search .......... 250/306, 307, 310, 311, 250/252.1 R; 378/71, 72; 73/760

[56] References Cited

U.S. PATENT DOCUMENTS

| | | | |
|---|---|---|---|
| 4,402,227 | 9/1983 | Hayashi et al. | 378/72 |
| 4,489,425 | 12/1984 | Borgonovi | 378/72 |
| 4,561,062 | 12/1985 | Mitchell | 378/72 |
| 4,686,631 | 8/1987 | Ruud | 378/72 |
| 4,709,383 | 11/1987 | Goto et al. | 378/72 |

OTHER PUBLICATIONS

Sewell et al, "High-Energy Electron-Diffraction and X-ray Emission Analysis of Surfaces and Their Reaction Products", Developments in Applied Spectroscopy, May 13-17 1968, pp. 61-79.

*Primary Examiner*—Bruce C. Anderson
*Attorney, Agent, or Firm*—Laurence Coit

[57] ABSTRACT

The degree of fatigue of a metallic material is determined by the linear relationship found to exist between the means angles of orientation deviation calculated from the electron diffraction patterns obtained by the selected field method and the degrees of fatigue. This method is justified because the mean angles determined near the fatigue crack and those determined at places removed therefrom differ only a little, meaning that determination of degree of fatigue can be conducted without being influenced by the location of sample taking.

2 Claims, 9 Drawing Sheets

ELECTRON DIFFRACTION METHOD OF DETERMINING THE DEGREE OF FATIGUE FOR METALLIC MATERIALS

BACKGROUND OF THE INVENTION

1. Technical Field

This invention relates to a method of determining the degree of fatigue for metallic materials that constitute structures or machine components, such as pressure vessel.

2. Background Art

A conventional and popular method of determining the degree of fatigue for metallic materials is to measure the half-value width of an approximately selected X-ray diffraction spectrum, the change in which being related to the degree of fatigue. However, there are problems in this method, such as, for example, the changes in said half-value width and the changes in the degree of fatigue are not linerary related as shown in FIG. 9; for another example, the half-value widths determined for cracked portion often differ greatly from those determined for parts away from the crack even for materials having expended their fatigue lifetimes, or of a degree of fatigue of 100%.

Although there are other methods available for estimating the degree of fatigue, such as by changes in the hardness and by those in the metallographic microstructure, none is accurate enough to be accepted generally.

SUMMARY OF THE INVENTION

A purpose of this invention is to offer a method of accurately determining the degree of fatigue for metallic materials. Other and incidental purposes of this invention will be clarified as it is disclosed.

According to this invention, plural number of electron diffraction patterns are taken by the selected field method from different fields of observation in the sample, and the mean of the angles of deviation in the orientation of these fields determined thusly is calculated therefrom; then the degree of fatigue of said sample is determined by comparing the mean angle of orientation deviation obtained above with a separately prepared table or characteristic correlation diagram that gives relationship existing between the mean angles of orientation deviation and the degrees of fatigue, from 0% to 100%, of the material concerned. Here, these values of mean angle of orientation deviation are calculated statistically.

Now, the mean angle of orientation deviation determined by aforesaid selected field method of electron diffraction has following properties:

1. it increases linearly with increasing degree of fatigue, or other forms of material damage; and
2. the differences between value obtained for a material of 100% fatigue at near the fatigue crack and those obtained at places removed therefrom are small.

Therefore, this method admits of accurately determining the degree of fatigue of a material without being influenced by the location of taking sample from said material.

DESCRIPTION OF THE PREFERRED EMBODIMENT

The present invention is now disclosed referring to attached drawings.

Firstly, the mean values of orientation deviation are calculated from the patterns obtained by the selected field method of electron diffraction for samples known to have fatigued to various degrees between 0% and 100%.

In the present embodiment, experiments were conducted for round rod test pieces machined out of a pressure vessel grade high strength steel SA 508 Class 3, and fatigued to 0% (this presenting the original state), 25%, 50%, 75%, and 100%.

Samples are taken from the test pieces prepared thusly, and the angles of orientation deviation are measured for these samples from electron diffraction patterns obtained by the selected field method. Here, a transmission electron microscope is used to arbitrarily choose an object area in the magnified image of the sample by means of a field selecting aperture device so that several cells are contained in aforesaid object area. A selected field electron diffraction pattern of this area is then recorded in a photographic plate. Subsequently, four more object areas are arbitarily selected as before by moving the aperture (five areas in all), and their diffraction patterns are recorded superimposed in the same photographic plate.

This procedure is repeated as many times as may be deemed necessary, but generally repetition of 15 to 20 times, each for a different part of the sample, is sufficient. Thus, a desired number of photographs of diffraction patterns are obtained, each bearing five diffraction patterns superimposed each other.

For each of the photographs, the largest angle of orientation deviation $\theta$ is determined, thus obtaining as many $\theta$'s as there are photographs. Then these $\theta$'s are plotted on a normal probability distribution graph, and their mean value $\mu$ is graphically determined.

This procedure is depicted in FIGS. 1 to 6, where the processing of data of angles of orientation deviation $\theta$ for samples taken from a part near the fatigue crack found in the aforesaid test pieces, namely those fatigued to 0%, 25%, 50%, 75%, and 100%, is shown. That is to say, the $\theta$ data are plotted on a normal probability distribution graph as a function of the probability ($=\{n/(N+1)\}\times 100(\%)$, where N is the number of the data, and n is an integer for ordering), whereby the mean value for the angle of orientation deviation $\mu$ is given by that value of $\theta$ on the correlation line which corresponds to a probability of 50% on the ordinate.

Here, the standard deviation $\sigma$ for the angles of orientation deviation $\theta$ is also obtained. Namely, in FIG. 1, the abscissa distance between the points a and b, defined on the correlation line as respectively corresponding to the levels $\mu$-mean and $\mu-\sigma$ on the ordinate, gives the $\sigma$.

Figure 1:
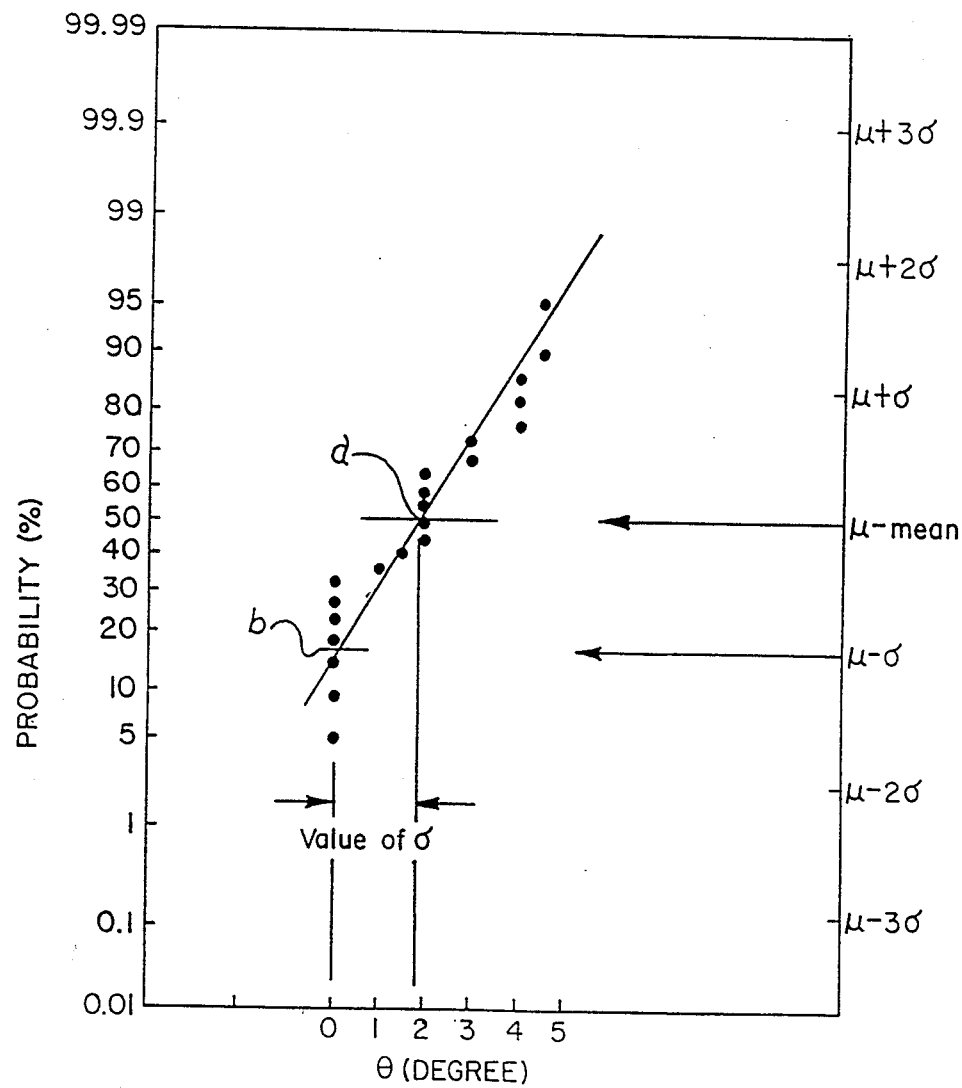
FIG. 1 is a drawing showing the angles of orientation deviation as plotted on a normal probability distribution graph to calculate the mean angle of orientation deviation for a 0% fatigued sample according to this invention.
Figure 2:
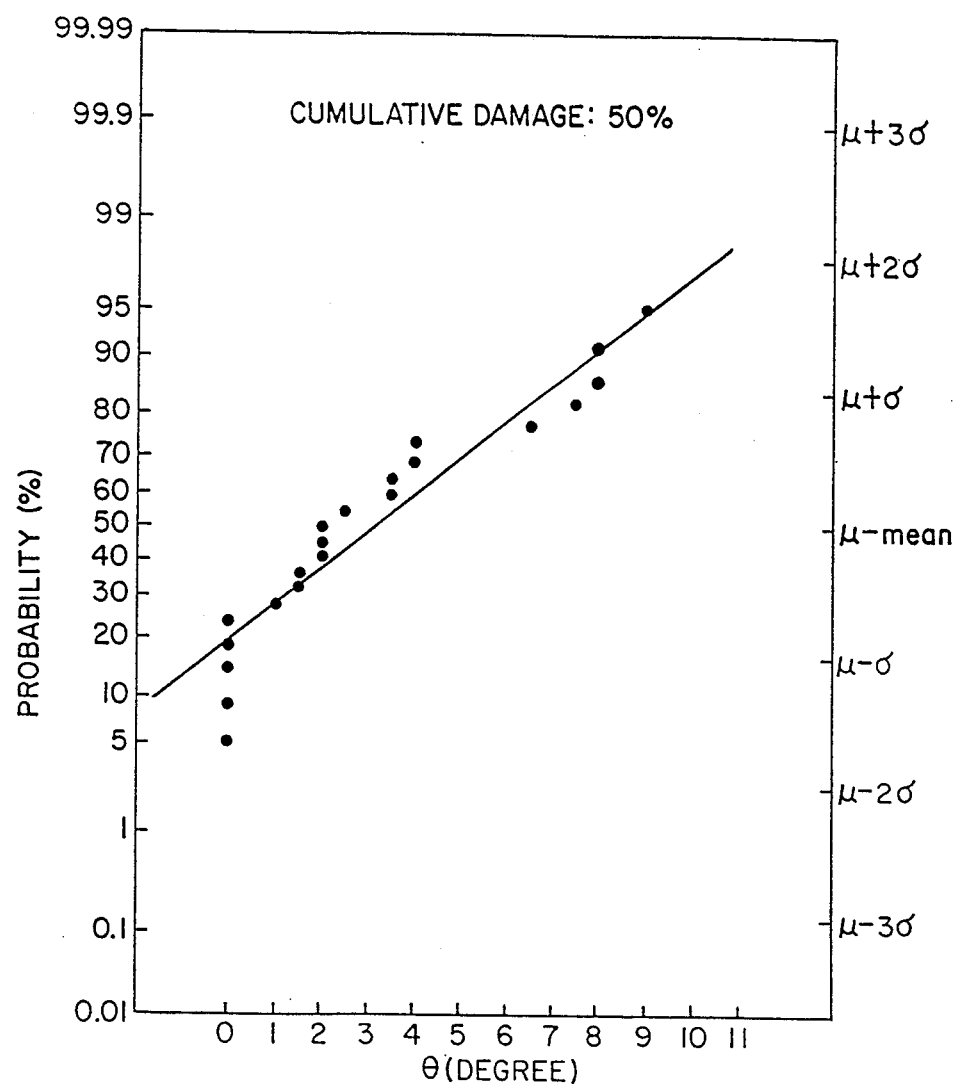
FIG. 2 is a graph prepared to calculate the mean angle of orientation deviation for a 25% fatigued sample.
Figure 3:
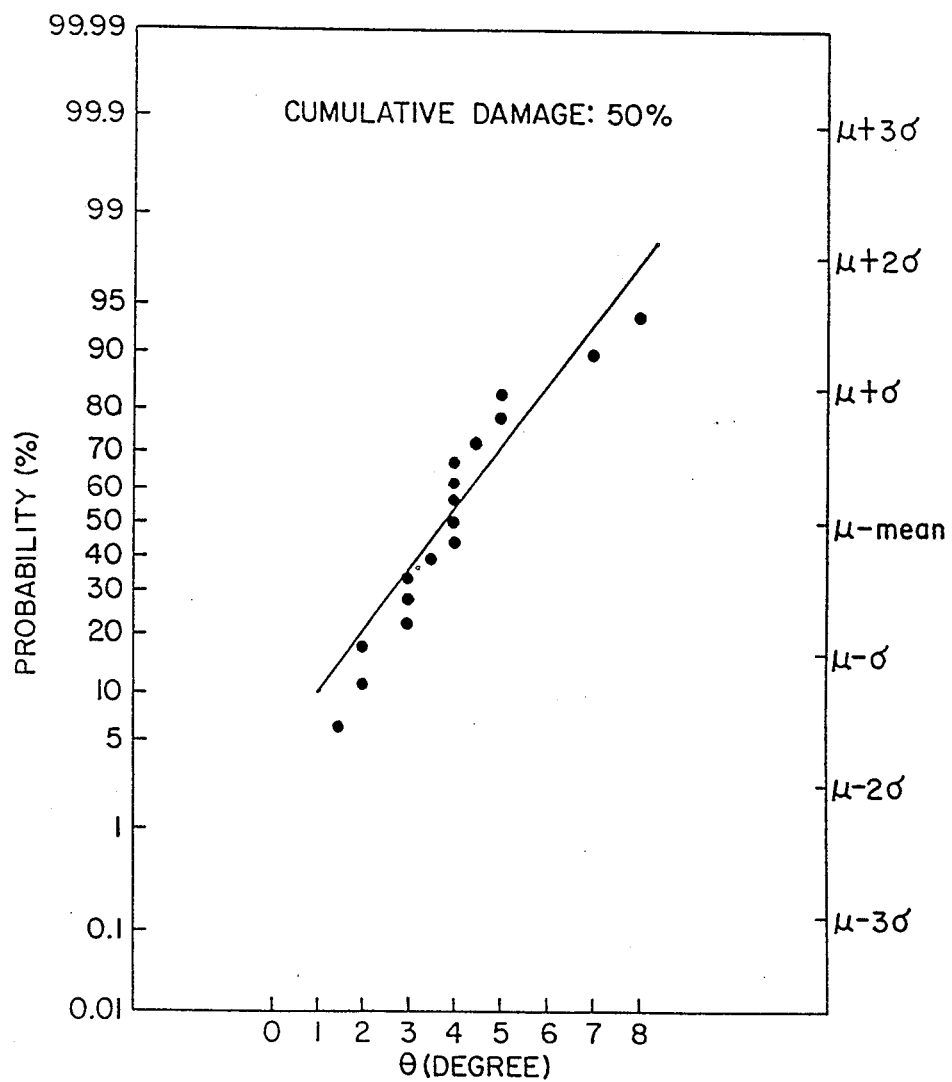
FIG. 3 is a graph prepared to calculate the mean angle of orientation deviation for a 50% fatigued sample.
Figure 4:
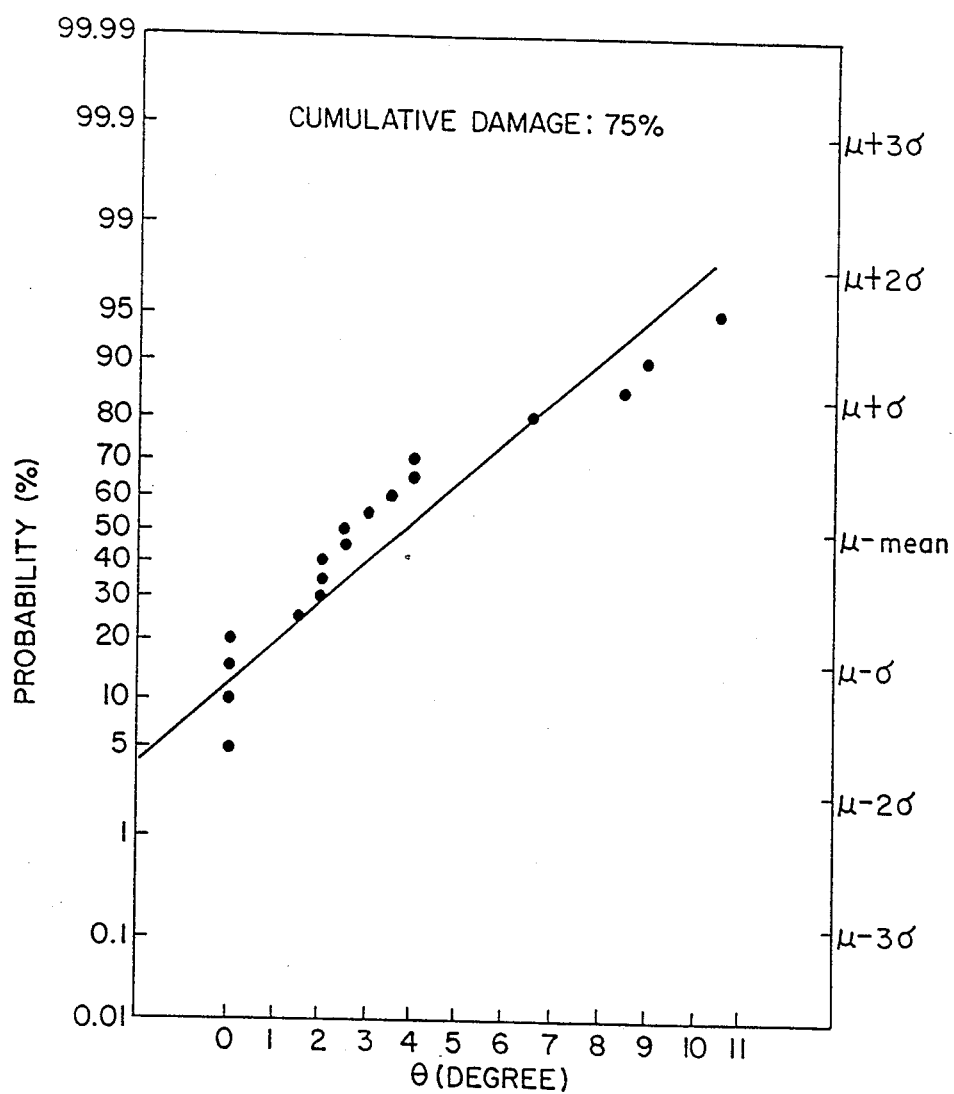
FIG. 4 is a graph prepared to calculate the mean angle of orientation deviation for a 75% fatigued sample.
Figure 5:
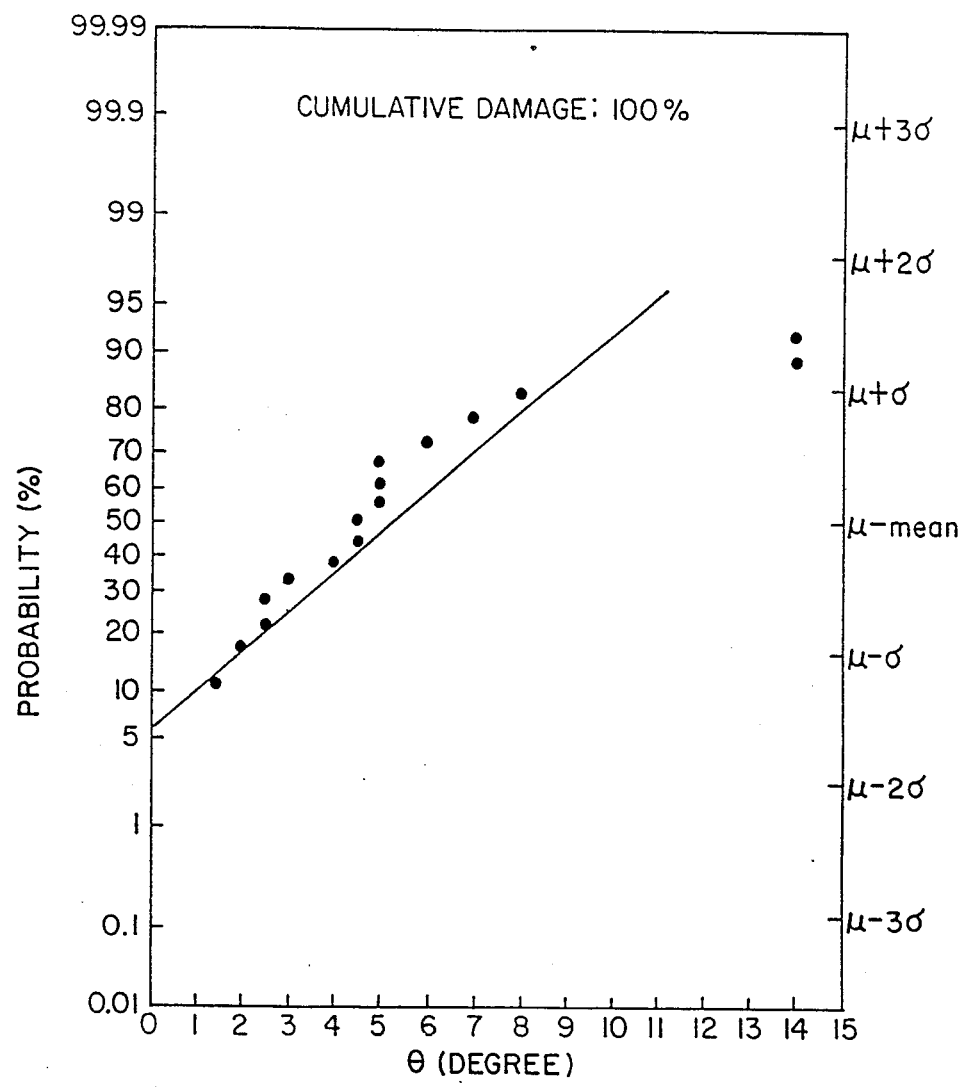
FIG. 5 is a graph prepared to calculate the mean angle of orientation deviation for a 100% fatigued angle.
Figure 6:
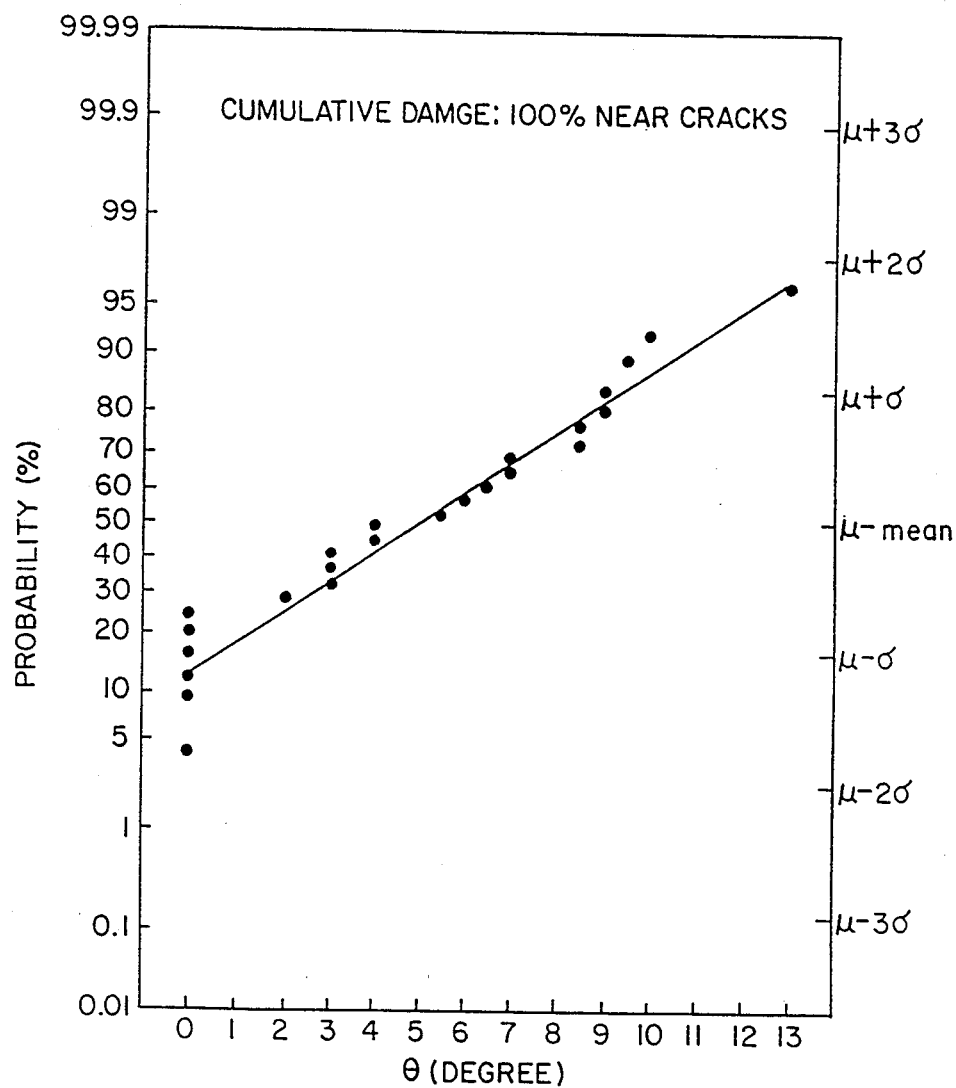
FIG. 6 is a graph prepared to calculate the mean angle of orientation deviation at near the fatigue crack for a 100% fatigued sample.
Figure 7:
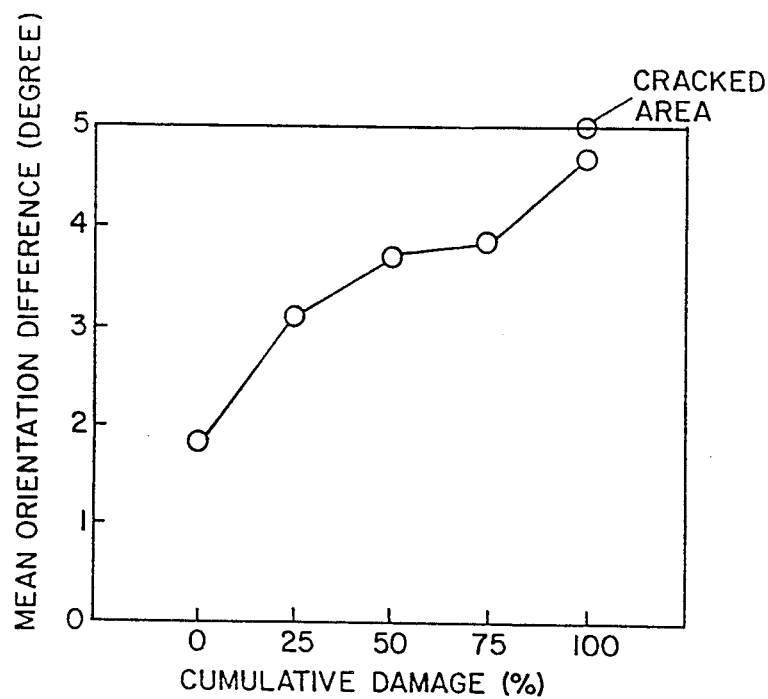
FIG. 7 is a graph showing the relationship of the mean angles of orientation deviation to the degrees of fatigue.

The mean values $\mu$ are shown in FIG. 7 against the degrees of fatigue for 0% to 100%. It will be appreciated that the mean values $\mu$ of the angles of orientation deviation $\theta$ are related to the degrees of fatigue approximately linearly, and that the difference in values obtained near the crack and at places removed therefrom is small. This demonstrates that it is indeed possible to determine the degree of fatigue (or the lifetime, either its whole value or what remained thereof) for a metallic material by comparing the mean angle of orientation deviation measured for said material and a graph established separately to give the relationship of aforesaid angles to the degrees of fatigue, such as FIG. 7.

Figure 8:
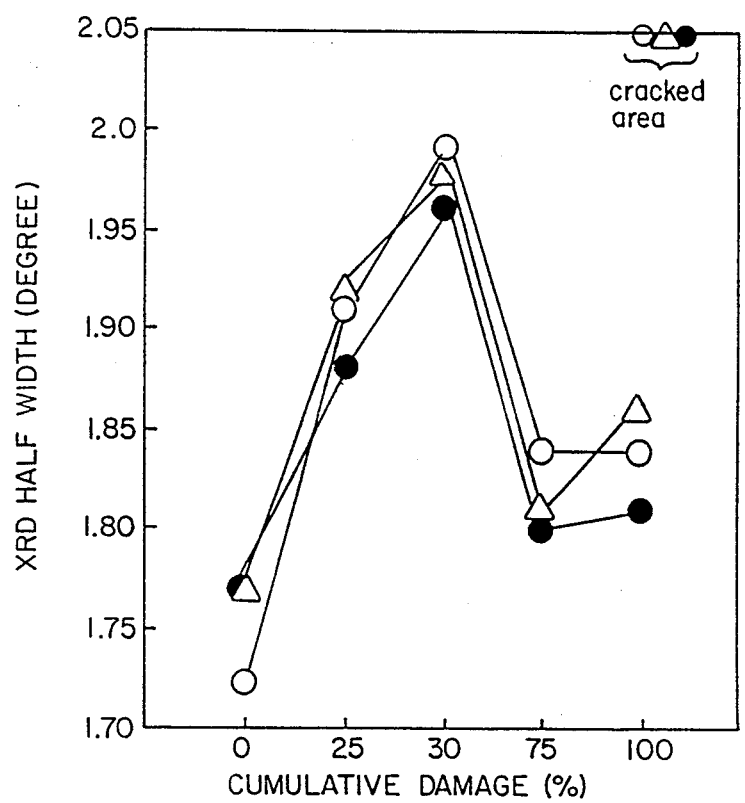
FIG. 8 is a graph showing the relationship of the standard deviations of the angles of orientation deviation to the degrees of fatigue.
Figure 9:
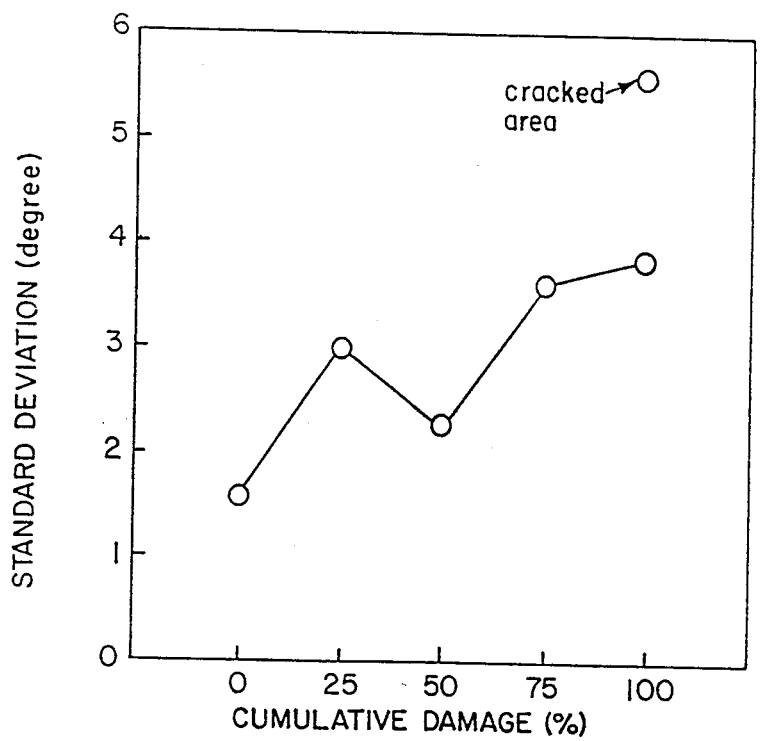
FIG. 9 is a graph showing the relationship of the half-value widths of an X-ray diffraction spectrum to the degrees of fatigue according to a conventional method of determining the degree of fatigue.

It will be noted in FIG. 8, furthermore, that the standard deviations of aforesaid angles of orientation deviation and the degrees of fatigue are also related approximately linearly. Therefore, this correlation may be utilized for determining the degree of fatigue as well as by aforesaid mean angles of orientation deviation themselves for the metallic material concerned. Also, cooperative application of these two relations may advantageously be employed.

We claim:

1. A method of determining the degree of fatigue for metallic materials comprising:

taking electron diffraction patterns by a selected field method for plural number of object areas, arbitrarily selected in a sample taken from the metallic material concerned;

calculating the mean angle of orientation deviation from the diffraction patterns obtained above; and comparing the mean angle of orientation deviation calculated above with the mean angles of orientation deviation separately determined for test pieces taken from the material concerned and fatigued to various degrees between 0% and 100%.

2. A method of determining the degree of fatigue for metallic materials according to claim 1, comprising:

taking electron diffraction patterns by said selected field method for plural number of object areas, arbitrarily selected in said sample taken from the metallic material concerned;

calculating the standard deviation of the angles of orientation deviation from the electron diffraction patterns; and comparing the standard deivation of the angles of orientation deviation calculated above with the standard deviations of the angles of orientation deviation separately determined for test pieces taken from the material concerned and fatigued to various degrees between 0% and 100%.

* * * * *